(12) United States Patent
Huang et al.

(10) Patent No.: US 9,913,701 B2
(45) Date of Patent: Mar. 13, 2018

(54) METHOD FOR DIGITAL ARCHIVING AND MANUFACTURING OF DENTAL PROSTHETICS AND PROSTHESIS, AND TEACHING AND TRAINING FOR SAME

(75) Inventors: Ta-Ko Huang, Kaohsiung (TW); Jerry T. Huang, Kaohsiung (TW)

(73) Assignees: EPED INC., Kaohsiung (TW); Jerry T. Huang, Kaohsiung (TW)

( * ) Notice: Subject to any disclaimer, the term of this patent is extended or adjusted under 35 U.S.C. 154(b) by 337 days.

(21) Appl. No.: 14/416,586

(22) PCT Filed: Jul. 23, 2012

(86) PCT No.: PCT/CN2012/079024
§ 371 (c)(1),
(2), (4) Date: Jan. 22, 2015

(87) PCT Pub. No.: WO2014/015459
PCT Pub. Date: Jan. 30, 2014

(65) Prior Publication Data
US 2015/0202027 A1 Jul. 23, 2015

(51) Int. Cl.
*A61C 13/00* (2006.01)
*A61C 5/77* (2017.01)
(Continued)

(52) U.S. Cl.
CPC ............ *A61C 13/0004* (2013.01); *A61C 5/77* (2017.02); *A61C 9/006* (2013.01); *A61C 9/0053* (2013.01);
(Continued)

(58) Field of Classification Search
CPC ..... A61C 11/00; A61C 13/34; A61C 13/0004; A61C 9/0053; A61C 9/006; A61C 13/0006; A61C 5/77; G09B 23/283
See application file for complete search history.

(56) References Cited

U.S. PATENT DOCUMENTS 8,047,846 B2 * 11/2011 Wen ...................... A61C 7/002
433/213
2002/0013636 A1 1/2002 O'Brien et al.
(Continued)

FOREIGN PATENT DOCUMENTS

CN 1585625 A 2/2005
CN 101450010 A 6/2009
(Continued)

*Primary Examiner* — Nicholas Lucchesi
(74) *Attorney, Agent, or Firm* — Leong C. Lei

(57) ABSTRACT

A method for digital archiving and manufacturing of dental prosthetics and a prosthesis, and teaching and training for the method are provided. The method mainly includes the following steps: preoperative scanning: creating a first digital model file; optical positioning and turning treatment: creating a second digital model file from a turning process; physical model calculation: creating reversely an autologous crown model file of a patient; and fixed denture manufacturing: manufacturing, according to the second digital model file and the autologous crown model file, a fixed denture that meets needs of the patient, so that an inner layer structure of a crown of the fixed denture can be tightly bound to an abutment, and it may be decided to retain an original crown contour according to needs. A tooth model based on a teaching digital model file can be used for teaching and training of a trainee with the foregoing method.

10 Claims, 4 Drawing Sheets

(51) Int. Cl.
　　　*G09B 23/28*　　　(2006.01)
　　　*A61C 9/00*　　　(2006.01)
　　　A61C 13/34　　　(2006.01)
　　　A61C 11/00　　　(2006.01)

(52) U.S. Cl.
　　　CPC ........ *A61C 13/0006* (2013.01); *G09B 23/283* (2013.01); *A61C 11/00* (2013.01); *A61C 13/34* (2013.01)

(56) References Cited

U.S. PATENT DOCUMENTS

| | | | |
|---|---|---|---|
| 2005/0142517 A1* | 6/2005 | Frysh | A61C 13/0004 433/173 |
| 2009/0042167 A1* | 2/2009 | Van Der Zel | A61C 1/084 433/215 |
| 2009/0148809 A1 | 6/2009 | Kuo et al. | |
| 2010/0105011 A1* | 4/2010 | Karkar | A61C 1/084 433/215 |
| 2011/0196654 A1* | 8/2011 | Genest | A61C 13/0004 703/1 |

FOREIGN PATENT DOCUMENTS

| | | |
|---|---|---|
| CN | 101689309 A | 3/2010 |
| CN | 102078225 A | 6/2011 |
| CN | 202005812 U | 10/2011 |

\* cited by examiner

METHOD FOR DIGITAL ARCHIVING AND MANUFACTURING OF DENTAL PROSTHETICS AND PROSTHESIS, AND TEACHING AND TRAINING FOR SAME

CROSS REFERENCE TO RELATED APPLICATIONS

This application is a 371 National Stage of PCT/CN2012/079024, filed on Jul. 23, 2012, for which priority is claimed under 35 U.S.C. § 119, the entire contents of all of which are hereby incorporated by reference.

BACKGROUND

Technical Field

The present invention relates to a method for digital archiving and manufacturing of dental prosthetics and a prosthesis, and teaching and training for manufacturing of dental prosthetics and a prosthesis.

Related Art

In dental caries treatment, when a permanent tooth is damaged, a new tooth no longer grows after the damaged permanent tooth is removed. Therefore, there is a kind of treatment referred to as prosthodontics, in which a fixed denture (commonly referred to as a crown and a bridge) is used, a natural tooth is ground through turning for use as an abutment tooth, and a fixed denture-crown or bridge that is made of metal or made of metal and ceramic is then bonded to the abutment tooth.

A crown is applicable when a conventional prosthodontic method cannot be used because of damages caused by severe tooth decay or external injuries or other reasons, and a tooth, after being properly ground through turning, is protected by the crown, so as to continue the use instead of being removed. For a tooth in which a root canal has been treated, because the tooth has severe defects, in addition to manufacturing a crown, an extra tooth core (commonly referred to as a nail) needs to be manufactured in the root canal to support the crown.

A bridge is applicable when a tooth is removed, and after teeth before and after an edentulous area are ground through turning, the edentulous area is repaired though a prosthesis in a similar way to bridging. In the edentulous area that is formed after the tooth is removed, overeruption is caused if the edentulous area stays empty for a long time, and mal-occlusion is also caused because the teeth before and after the edentulous area leans teeth (abutment).

The conventional method of prosthesis is: duplicating a dental cast from a patient by using gypsum after the turning treatment; carving a crown manually with an occlusion device. In the wake of performing occlusal adjustment by hand, a hand-made crown will be duplicated in the end. This traditional way is not only a time-consuming process, but also requires human power.

A current trend in dentistry is introduced by a computer-aided design (CAD)/computer-aided manufacturing (CAM) system. The concept is derived from the industry of mechanical manufacturing. Scanning into the oral cavity is mainly performed through an intraoral scanner after the turning treatment. For example, computed tomography (CT) photography can provide internal anatomical information, including teeth, jawbones, alveolar nerves, upper sinuses, and so on. The patient's data is generated based on a digital 3D environment, then a digital crown is selected and used, a digital file of the crown is completed through virtual occlusion adjustment (this process is similar to CAD). Next, the replacement tooth is directly produced through automatic turning by using a milling machine. The introduction of this process speeds up the manufacture of dental.

Because the dental CAD/CAM system is in a state of developing, and also some reasons like immaturity or cost; there are cases of incomplete introduction. Therefore, the third manner that combines a conventional method with CAD/CAM comes out. The third manner mainly includes: duplicating a dental cast for a patient after turning treatment, scanning the dental cast, generating dental cast data of the patient based on a digital 3D environment, then selecting and using a digital crown; completing a digital file of the crown through virtual occlusion adjustment, and finally producing a false tooth directly through automatic turning by using a processing machine. The introduction of this process can speed up manufacturing of a false tooth.

However, the foregoing methods of manufacture a fixed denture-crown or bridge are all based on that. An abutment tooth after the restoration treatment is used as a base for duplicating the dental cast or having an intraoral scanning from the patient's mouth. Both the conventional manufacturing method and the use of a dental CAD/CAM system, have a problem that an abutment and a crown can't be tightly bound; moreover, a bridge does not use a contour of an original tooth of the patient, and instead uses a crown carved by a technician or a crown in a database, causing that a physician or a patient cannot decide, according to needs, whether to retain an original crown or use a crown model created in a database.

SUMMARY

In order to solve the foregoing defect, an objective of the present invention is to provide a method for digital archiving and manufacturing of dental prosthetics and a prosthesis, and teaching and training for same, in which a whole process of turning a tooth of a patient is recorded through creating a digital model and using a manner of optical space 3D positioning, all teeth removed through turning and remaining abutments are recorded, and a crown is directly manufactured by using such data, so as to achieve tight bonding between a crown and an abutment.

In order to achieve the foregoing objective, the present invention discloses a method for digital archiving and manufacturing of dental prosthetics and a prosthesis, and the method mainly includes the following steps: preoperative scanning: performing preoperative contour scanning on a to-be-treated tooth of a patient by using a scanning device, so as to create a first digital model file; optical positioning and turning treatment: combining turning tool optical positioning with the first digital model file in a manner of tracking a medical apparatus by using an optical positioning system, turning the to-be-treated tooth into an abutment tooth, and creating a second digital model file from a turning process; physical model calculation: creating reversely, by using the second digital model file created previously from the turning process, an autologous crown model file of the patient from a process of turning the to-be-treated tooth into the abutment tooth; and fixed denture manufacturing: manufacturing, by using CAD and CAM and according to the second digital model file and the autologous crown model file, a fixed denture that meets needs of the patient, where the fixed denture includes a crown and a bridge.

The preoperative scanning includes: first duplicating a dental cast of the patient by using plaster, and then sending the dental cast into a dental cast scanner to obtain the first digital model file, where the dental cast scanner includes an optical scanning device such as a laser optical scanning device or a projection optical scanning device.

The scanning device for preoperative scanning includes an intraoral scanning device, which directly performs photographing by using a sensor entering the mouth of the patient, and the first digital model file is created after a tooth contour is obtained.

The preoperative scanning is to directly photograph tomographic data in the mouth of the patient by applying CT photography, where the tomographic data includes information such as tooth contour, bone quality, neural tubes, and is used for creating the first digital model file.

The fixed denture manufacturing includes: determining inner and outer layer structures of a crown according to the second digital model file and the autologous crown model file, and then producing the fixed denture through automatic turning by using a tool.

The fixed denture manufacturing further includes crown selection: selecting, from a crown database by using software, a digital crown model file consistent with the patient; performing digital virtual occlusion adjustment after the digital crown model file consistent with the patient is selected; and determining inner and outer layer structures of a crown according to the digital crown model file and the autologous crown model file after the digital virtual occlusion adjustment is performed, and then producing the fixed denture through automatic turning by using a tool.

The method of the present invention may also be used for teaching and training for digital archiving and manufacturing of dental prosthetics and a prosthesis, which mainly includes the following steps: obtaining, by a trainee, a tooth model for which a teaching digital model file has been created; combining turning tool optical positioning with the teaching digital model file in a manner of tracking a medical apparatus by using an optical positioning system, turning the tooth model into an abutment tooth, and creating a second digital model file from a turning process; physical model calculation: creating reversely, by using an original crown contour file of the tooth model and the second digital model file, a crown model file from a process of turning the tooth model into the abutment tooth; fixed denture manufacturing: and producing a needed fixed denture by using the crown model file and using CAM; and sleeving the fixed denture on the abutment tooth, and evaluating results of turning and of manufacturing the fixed denture of the trainee.

Advantages of the present application lie in that: A digital model of an original tooth of a patient is created through preoperative scanning, and a manner of optical space 3D positioning is used, so that a whole process of turning the tooth of the patient is recorded and all teeth removed through turning and remaining abutments are recorded; a use process is stored, so as to facilitate practice and improvement in the future based on neglects and mistakes in the use process; and meanwhile such data may be used directly for production by an existing fixed denture manufacturing system, so as to achieve tight bonding between an inner layer structure of a crown and an abutment. Moreover, because there is an autologous crown model file, instead of using a crown carved by a technician or a crown in a database, the patient may directly use a contour of the original tooth, and occlusion adjustment is no longer needed, so that a physician or a patient has more than one choices and can decide, according to needs, whether to retain an original crown or use a crown created in a database.

BRIEF DESCRIPTION OF THE DRAWINGS

The disclosure will become more fully understood from the detailed description given herein below for illustration only, and thus are not limitative of the disclosure, and wherein.

DETAILED DESCRIPTION

Detailed content and technical explanations related to the present invention are now described in further detail with reference to the embodiments. However, it should be understood that the embodiments are only used for exemplary description, but should not be construed as a limit to the implementation of the present invention.

Figure 1:
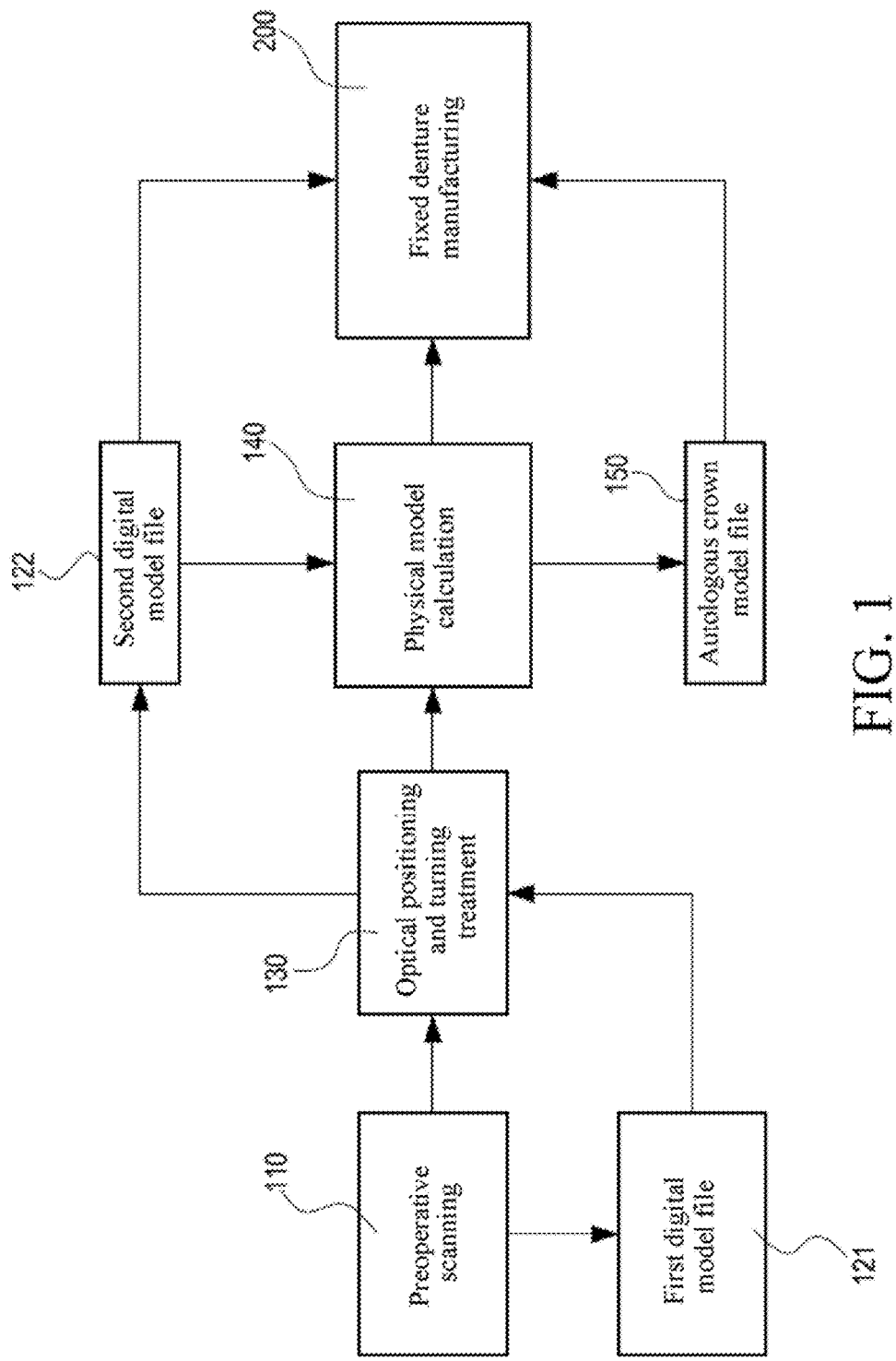
FIG. 1 is a schematic diagram 1 of an implementation process according to the present invention.
Figure 2:
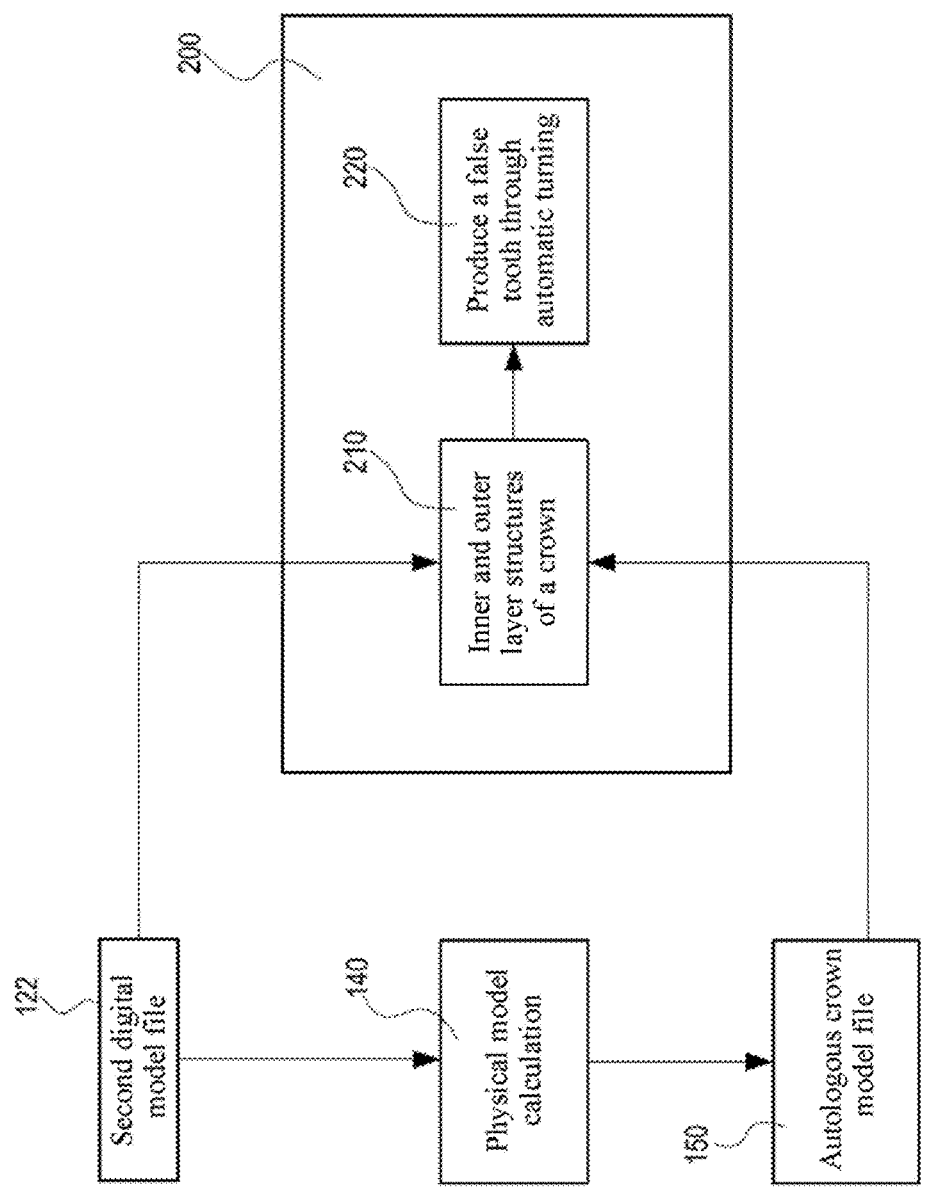
FIG. 2 is a schematic diagram 2 of an implementation process according to the present invention.

Referring to FIG. 1 and FIG. 2, the present invention discloses a method for digital archiving and manufacturing of dental prosthetics and a prosthesis, and the method mainly includes the following steps: preoperative scanning 110: performing preoperative contour scanning on a to-be-treated tooth of a patient by using a scanning device, so as to create a first digital model file 121.

The preoperative scanning 110 includes: first duplicating a dental cast of a patient by using plaster by using a conventional manufacturing method, and then sending the dental cast into a dental cast scanner to obtain the first digital model file 121, where the known dental cast scanner includes an optical scanning device such as a laser optical scanning device or a projection optical scanning device. The scanning device for preoperative scanning 110 also includes an intraoral scanning device, the intraoral scanning device directly performs photographing by using a sensor entering the mouth of the patient, and the first digital model file 121 is created after a tooth contour is obtained.

Alternatively, the preoperative scanning 110 is to directly photograph in the patient's mouth by applying CT photography, the tomographic data includes information such as tooth contour, bone quality, neural tubes, and is used for creating the first digital model file 121. If the scanning is performed in a CT manner, the information of the oral construction will provide more sufficiently so it could meet the demand of security in dental surgeries and which is more dependable than the intraoral scanner. The foregoing dental cast scanner, intraoral scanning device, and CT photography are existing technologies, and are not main parts of the present patent, and no further details are provided herein again.

After the preoperative scanning 110, optical positioning and turning treatment 130 are then performed. Turning tool optical positioning is combined with the first digital model file 121 in a manner of tracking a medical apparatus by using an optical positioning system, the to-be-treated tooth is turned into an abutment tooth, and a second digital model file 122 is created from a turning process. The optical positioning and turning treatment 130 are mainly to record a whole process of tooth turning in a manner of space 3D positioning. When a mistake occurs during a turning, the warnings will display. In addition to achieving safe and precise turning, a fixed denture-crown can be made by the data which recorded all the removed (during the turning) and remaining teeth (abutment teeth).

A manner of tracking a medical apparatus by using an optical positioning system is an existing technology. For example, in U.S. Pat. No. 6,675,040, entitled "Optical Object Tracking System", an optical detection system is disclosed. The optical detection system is used for recording a spatial position of an instrument connected to an optically detectable object, and can search for positions of an instrument, a target, a patient, and an apparatus during an operation, diagnosis, and treatment settings by combining multiple cameras with data processors, image scanning data, and a computer-related graphic display. Related progressive technologies are disclosed in the market later. So the technologies of tracking a medical apparatus by using an optical positioning system are known technologies, and are not main points of the present patent, and no further details are provided herein again.

After the optical positioning and turning treatment 130, physical model calculation 140 is then performed, and an autologous crown model file 150 of the patient is created reversely by using the second digital model file 122 created previously from the process of turning the to-be-treated tooth. The autologous crown model file 150 is generated from the turning data of all the teeth removed through turning and the remaining teeth (abutment teeth), including a contour of the crown and an inner structure that is joined with the abutment tooth.

After the physical model calculation 140, because the autologous crown model file 150 is generated by recording data of all the teeth removed through turning and the remaining teeth (abutment teeth), such data can be directly used for fixed denture manufacturing 200. In the fixed denture manufacturing 200, inner and outer layer structures of a crown 210 are determined by using CAD and CAM of a false tooth turning tool system and according to the second digital model file 122 and the autologous crown model file 150, a false tooth through automatic turning by using a tool is then produced 220, and a fixed denture that meets the needs of the patient is manufactured. A fixed denture includes a crown and a bridge.

Figure 3:
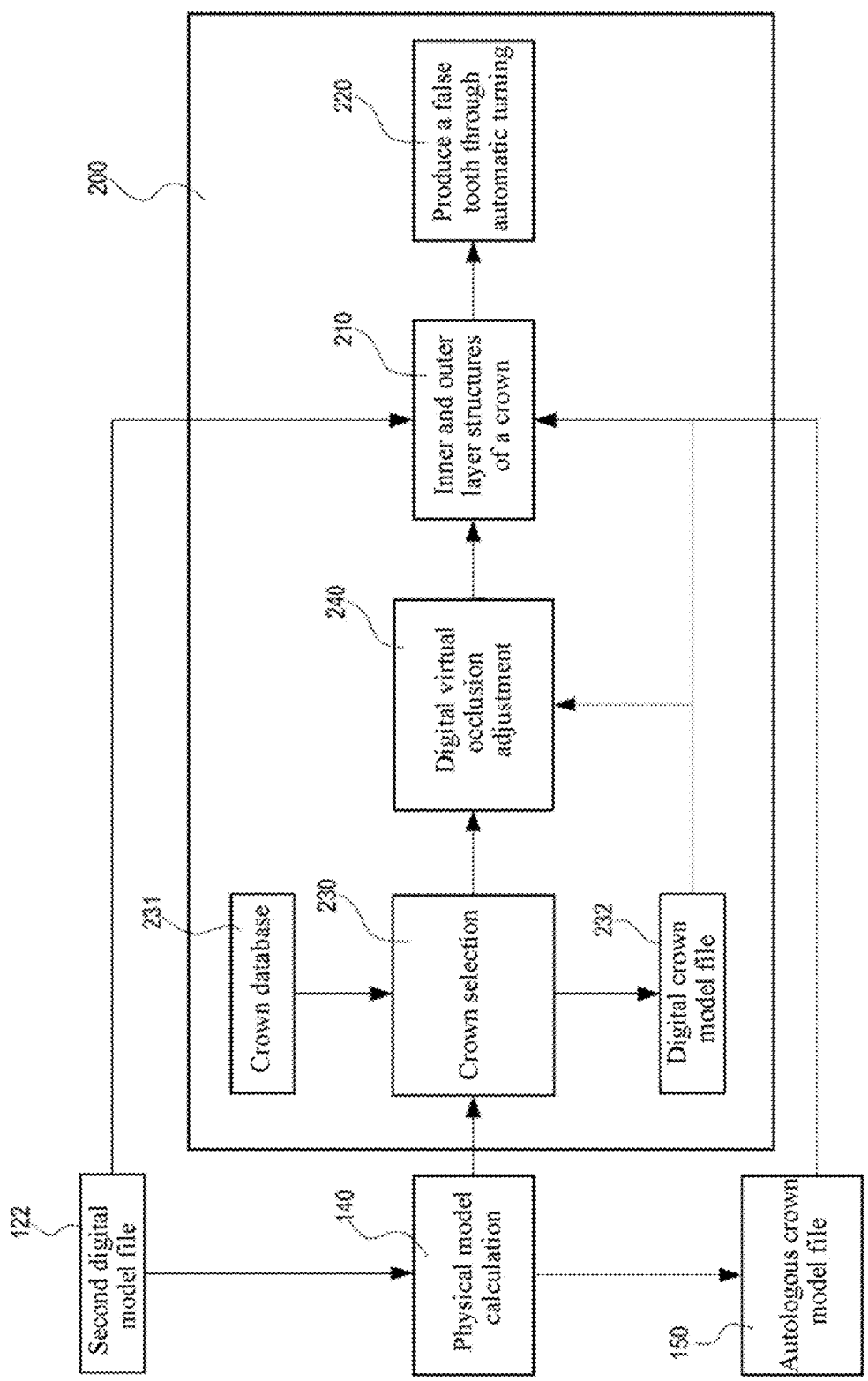
FIG. 3 is a schematic diagram 3 of an implementation process according to the present invention.

Refer to FIG. 3, the fixed denture manufacturing 200 further includes crown selection 230. The crown selection 230 is performed when a physician or patient does not use a contour of an original tooth, or a contour of an original tooth cannot be recognized and used, a digital crown model file 232 consistent with the patient is selected from a crown database 231 by using software; after the digital crown model file 232 which is consistent with the patient is selected, digital virtual occlusion adjustment 240 is performed by using a known method for simulating a crown from a tooth occlusion curved surface; and after the digital virtual occlusion adjustment 240 is performed, the inner and outer layer structures of the crown 210 are determined according to the digital crown model file 232 and the autologous crown model file 150, a false tooth is then produced through automatic turning by using a tool 220, and a fixed denture which meets the needs of the patient is manufactured, where the fixed denture includes a crown and a bridge.

Figure 4:
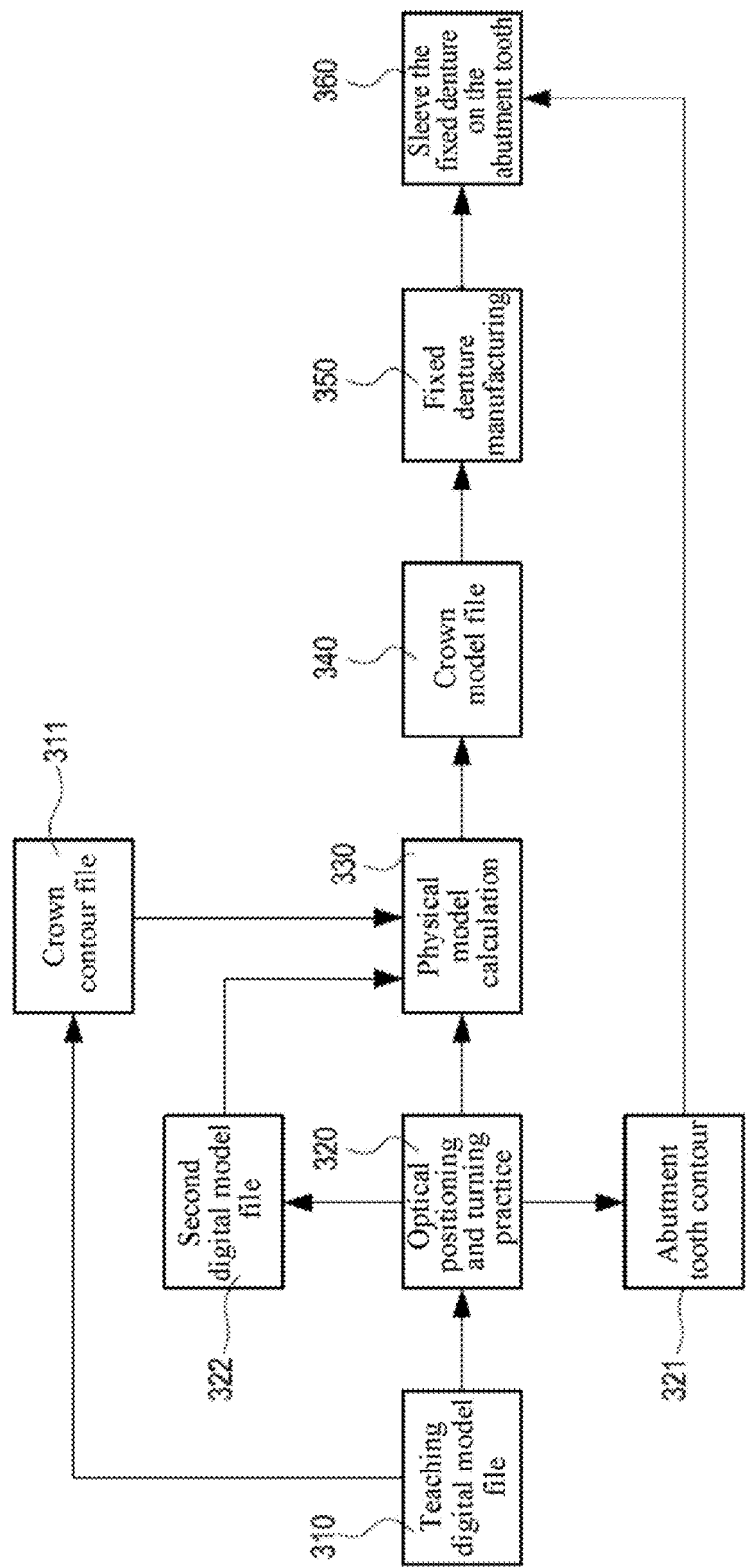
FIG. 4 is a schematic diagram of a process of teaching and training according to the present invention.

Refer to FIG. 4, the method above may be used for teaching and training the product of a fixed denture, which mainly includes the following steps: obtaining, by a trainee, a tooth model for which a teaching digital model file 310 has been created, where the teaching digital model file 310 may be a tooth model of a standard tooth, or created through duplicating a tooth model of a patient by using plaster, and a forming manner of the teaching digital model file 310 may be a creating manner of the foregoing first digital model file 121, or may be created according to general standards of teachers.

Next, optical positioning and turning practice 320 is performed, and same as the above, combine turning tool optical positioning with the teaching digital model file 310 in a manner of tracking a medical apparatus by using an optical positioning system, the tooth model is turned into an abutment tooth contour 321; and the second digital model file 322 is created from a turning process.

After the optical positioning and turning practice 320, physical model calculation 330 is performed then. The crown model file 340 is created reversely, by using an original crown contour file 311 of the tooth model in the teaching digital model file 310 and the second digital model file 322, from a process of turning the tooth model into the abutment tooth, and the crown model file 340 is about inner and outer layer structures of a crown that are determined according to the second digital model file 322 and the original crown contour file 311.

Next, the fixed denture manufacturing 350 is produced according to the crown model file 340. A needed fixed denture is produced by using CAM, and the fixed denture includes either a crown or a bridge.

Finally, the fixed denture is sleeved on the abutment tooth 360. In this step, the results of turning and manufacturing the fixed denture of the trainee may be evaluated. Also, digital and physical examinations may be performed according to the second digital model file 322 created from the turning process.

The above descriptions are merely preferred to embodiments of the present invention which are not intended to limit the scope of implementation of the present invention. Any simple equivalent change or modification made according to the content of the claims and specification of the present invention shall fall within the patent scope of the present invention.

What is claimed is:

1. A method for digital archiving and manufacturing of dental prosthetics and a prosthesis, wherein the method comprises the following steps:
    preoperative scanning: performing preoperative contour scanning on a to-be-treated tooth of a patient by using a scanning device, so as to create a first digital model file;
    optical positioning and turning treatment: using an optical positioning system to perform optical positioning of turning tool and then combining the turning tool with the first digital model file by tracking a medical apparatus by using the optical positioning system, cutting a tooth into an abutment tooth, and creating a second digital model file from cutting process;
    physical model calculation: creating reversely, by using the second digital model file created previously from the cutting process, an autologous crown model file of the patient from the process of cutting the tooth into the abutment tooth; and
    fixed denture manufacturing: manufacturing, by using computer-aided design (CAD) and computer-aided manufacturing (CAM) and according to the second digital model file and the autologous crown model file, a fixed denture that meets needs of the patient.

2. The method according to claim 1, wherein the preoperative scanning comprises: first duplicating a dental cast of the patient by using plaster, and then sending the dental cast to a dental cast scanner to obtain the first digital model file.

3. The method according to claim 2, wherein the dental cast scanner comprises a laser optical scanning device or a projection optical scanning device.

4. The method according to claim 1, wherein the scanning device for preoperative scanning comprises an intraoral scanning device which directly performs photographing by using a sensor entering the mouth of the patient, and the first digital model file is created after a tooth contour is obtained.

5. The method according to claim 1, wherein the preoperative scanning is to create the first digital model file by applying computed tomography (CT) photography.

6. The method according to claim 1, wherein the fixed denture comprises either a crown or a bridge.

7. The method according to claim 1, wherein the fixed denture manufacturing comprises: determining inner and outer layer structures of a crown according to the second digital model file and the autologous crown model file, and then producing the fixed denture through automatic turning by using a tool.

8. The method according to claim 1, wherein the fixed denture manufacturing further comprises crown selection: selecting, from a crown database by using software, a digital crown model file which is consistent with the patient.

9. The method according to claim 8, wherein, after the digital crown model file consistent with the patient is selected, digital virtual occlusion adjustment is performed.

10. The method according to claim 9, wherein, after digital virtual occlusion adjustment is performed, inner and outer layer structures of a crown are determined according to the digital crown model file and the autologous crown model file, and the fixed denture is produced through automatic turning by using a tool.

* * * * *